United States Patent [19]

Discko, Jr.

[11] Patent Number: 5,199,567
[45] Date of Patent: Apr. 6, 1993

[54] SINGLE PATIENT DOSE DENTAL CARTRIDGE TRAY AND ORGANIZING SYSTEM

[75] Inventor: John Discko, Jr., Hamden, Conn.

[73] Assignee: Centrix, Inc., Shelton, Conn.

[21] Appl. No.: 697,253

[22] Filed: May 8, 1991

[51] Int. Cl.$^5$ .............................................. B65D 83/10
[52] U.S. Cl. .................................... 206/369; 206/63.5; 206/368; 206/563; 206/564
[58] Field of Search ...................... 206/63.5, 368, 369, 206/370, 372, 373, 483, 486, 562, 563, 564; 433/77, 79

[56] References Cited

U.S. PATENT DOCUMENTS

| | | | |
|---|---|---|---|
| 3,013,656 | 12/1961 | Murphy | 206/563 |
| 3,308,962 | 3/1967 | Bryant | 206/459 |
| 3,589,511 | 6/1971 | Britt | 206/564 |
| 3,746,161 | 7/1973 | Jones | 206/564 |
| 4,153,160 | 5/1979 | Leigh | 206/370 |
| 4,340,140 | 7/1982 | Wilcox et al. | 206/373 |
| 4,353,694 | 10/1982 | Pererin | 206/63.5 |
| 4,420,085 | 12/1983 | Wilson et al. | 206/564 |
| 4,645,079 | 2/1987 | Hill | 206/564 |
| 4,736,850 | 4/1988 | Bowman et al. | 206/564 |
| 4,892,481 | 1/1990 | Kopunek et al. | |
| 4,915,233 | 4/1990 | Smith | 206/564 |

Primary Examiner—David T. Fidei
Attorney, Agent, or Firm—Paul A. Fattibene; Arthur T. Fattibene

[57] ABSTRACT

A dental tray for counting, storing, shipping and dispensing cartridges that includes a plurality of integrally formed wells for securely holding and sealing a dental cartridge which are placed horizontally within the wells in a manner whereby the discharge nozzle of the cartridge is positioned so that it abuts a portion of the well for sealing it from contamination and which the tray may be formed of opaque or color material which will block curing rays when light activated material is placed within the dental cartridges. Each cartridge is individually retained within its respective well by a snap or friction fit. A sliding or rotating cover is provided which is spaced slightly above the cartridges so as to prevent unintentional dislodgement of the cartridge from its well or seat. Identifying indicia relating to the color or shade of material contained within the cartridges therein can be readily applied to the tray and/or cartridge and which trays can be readily incorporated into a rack system and organized for the convenience of the dentist.

15 Claims, 8 Drawing Sheets

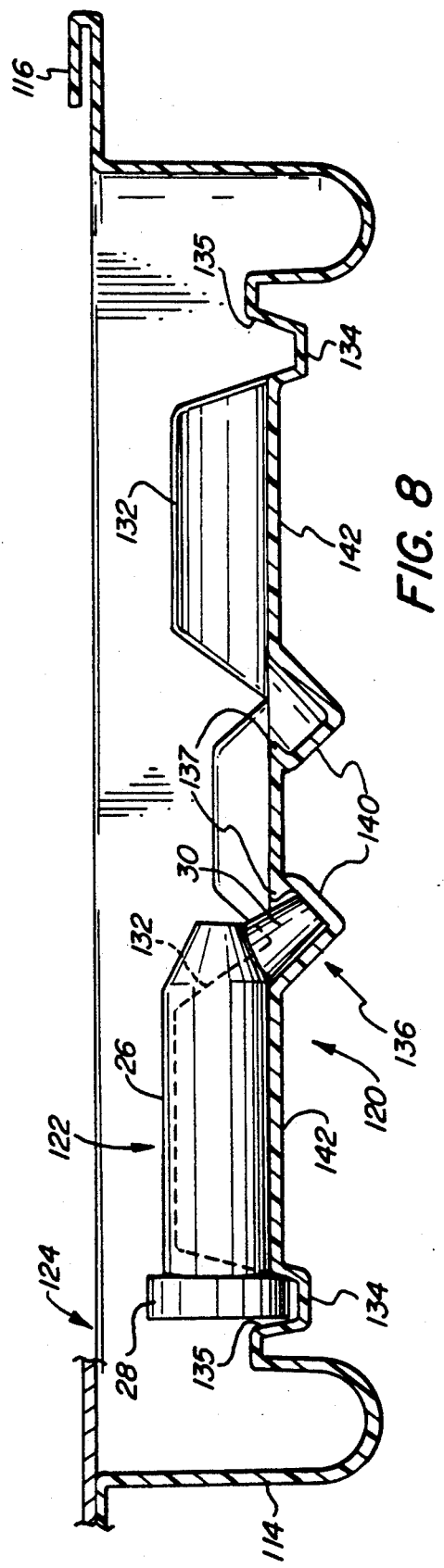
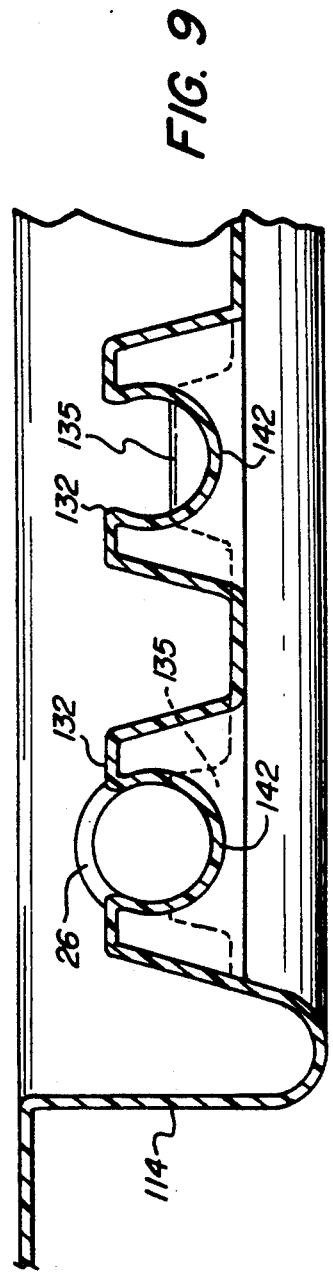
FIG. 8
FIG. 9

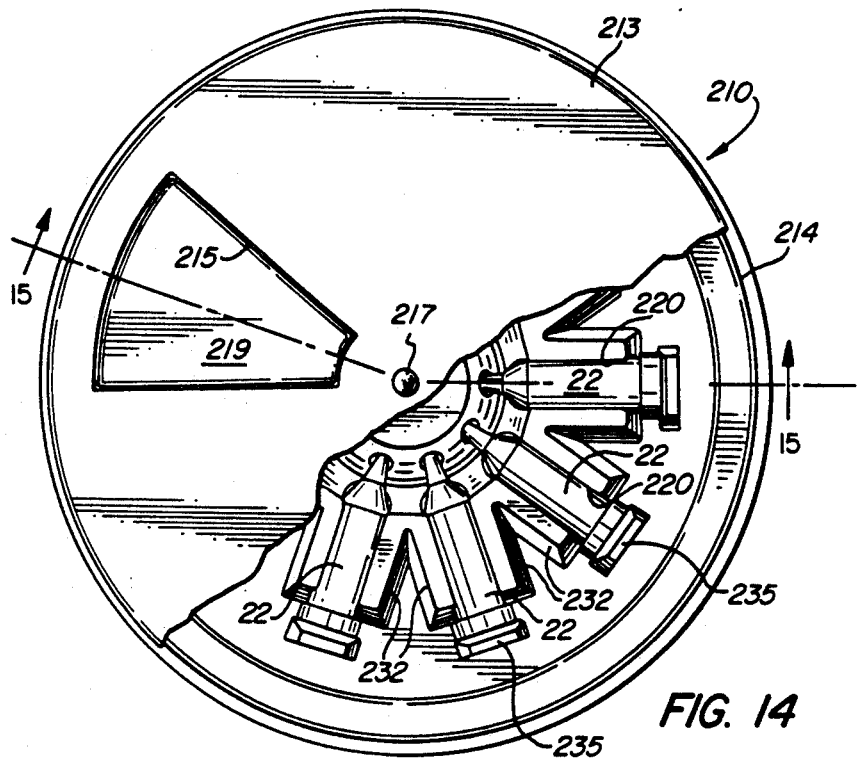
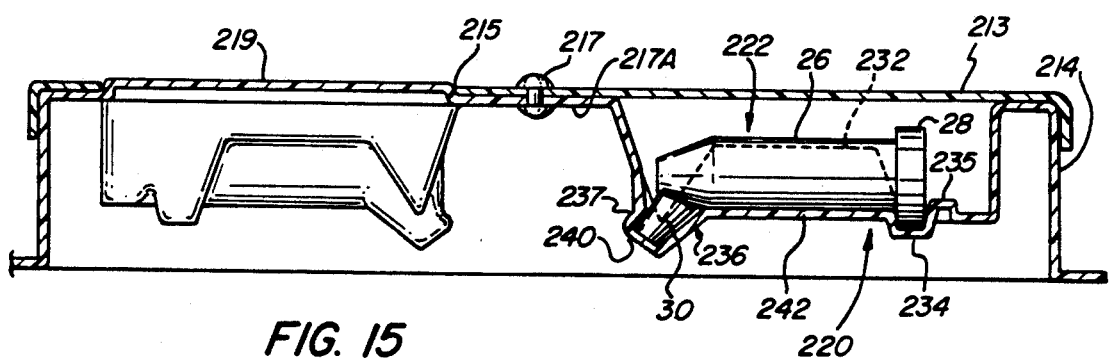
FIG. 14
FIG. 15

SINGLE PATIENT DOSE DENTAL CARTRIDGE TRAY AND ORGANIZING SYSTEM

FIELD OF THE INVENTION

This invention relates generally to packaging, and more particularly to packaging of single patient dose cartridges containing composite filling material as used in dentistry.

BACKGROUND OF THE INVENTION

In dentistry, it is now widely accepted practice to use unit dose cartridges for dispensing dental materials to dental patients. These cartridges are designed to contain a small dose of material that can be applied to a single patient. These single patient dose cartridges provide many advantages over other bulk dispensing techniques. For example, the application of dental filling material with a single dose dental cartridge permits a cavity to be filled from the inside out. This effectively prevents voids and the entrapment of air, which could compromise the integrity of the filling. Additionally, the use of a unit dose cartridge helps to prevent the risk of possible cross-contamination from one dental patient to the next. A single patient dose cartridge is used only on one patient and thereafter discarded. The single patient dose cartridge is also a convenience for the dentist. This saves the dentist valuable time. Also, the single patient dose cartridge is the only practical means, when made of an opaque actinic material, to apply light activated dental materials.

The cartridges are typically dispensed with the use of a syringe gun having a mechanical advantage. One example of a syringe used in conjunction with a cartridge is disclosed in U.S. Pat. No. 3,581,399 entitled "Composite Resin Filling Syringe and Technique" issuing to Dragan on Jun. 1, 1971. Another example of such a gun used with dental cartridges is disclosed in U.S. Pat. No. 4,198,756 entitled "Manual Extruder" issuing to Dragan on Apr. 22, 1980. Yet another syringe gun is disclosed in U.S. Pat. No. 4,384,853 entitled "Ejector Holder for Capsule Like Cartridge" issuing to Welsh on May 24, 1983.

A type of cartridge that is used in the syringe guns identified above is disclosed in U.S. Pat. No. 4,330,280 entitled "Ejector Holder for Capsule Like Cartridges" issuing to Dougherty et al on May 18, 1982. Yet another type of cartridge is disclosed in U.S. Pat. No. 4,963,093 entitled "Dental Syringe Tip and Syringe Holder Therefor" issuing to Dragan on Oct. 16, 1990, which is herein incorporated by reference. These cartridges typically have a reservoir body portion sealed at one end with a plug or piston, and an angularly disposed nozzle through which the dental material is discharged. The cartridges being disposable, are typically supplied in quantity. They are often packaged loosely together. To prevent contamination of the dental material contained therein, a sealing cap is placed over the discharge nozzle.

In manufacturing, the placement of the cap is often accomplished by a manual operation that requires some degree of dexterity to perform rapidly. The placement of the sealing cap may be accomplished by automation, but at a considerable expense. It is common practice to use color coding for these sealing caps to distinguish between colors or shades of colors of the dental material contained in the cartridge. However, as the numbers of colors and shades of dental material made available to the dentist increase, providing a successful color coding scheme for the sealing caps that can distinguish between the many colors and shades, is impractical. Additionally, when the loose cartridges are sealed with sealing caps, they must then be counted and repackaged for shipment to the dentist. This results in an additional step in the manufacturing process. Therefore, there is a need to improve the packaging of single patient dose cartridges to increase efficiencies and thereby reduce cost to the dentist, while at the same time providing a convenient package and system which the dentist can use for dispensing composite filling material in numerous shades and colors, resulting in improved dental care being provided to the patient.

SUMMARY OF THE INVENTION

The present invention is directed to a tray used for counting, packaging, storing and dispensing single patient dose cartridges used in dentistry. A tray is formed having a plurality of wells adapted to receive a single patient dose cartridge of the type having a reservoir body with a flange, and an angularly disposed nozzle. A flexible portion of the tray receives the body of the cartridge holding it securely in place. Another portion of the tray is adapted to receive the unsealed nozzle end of the cartridge. The portion of the tray receiving the nozzle end effectively seals the cartridge from contamination and exposure to light. A sliding top is used to cover the plurality of cartridges after placement in the tray, further protecting them. Identifying indicia is placed on the cover and tray to identify the type, color, or shade of material contained in the cartridges therein. The trays are organized in a rack system.

Therefore, it is an object of the present invention to provide efficient packaging for single patient dose cartridges used in dentistry.

It is a further object of the present invention to provide a packaging system that is convenient for the dentist.

It is an advantage of the present invention that the angularly disposed nozzle end of a single patient dose cartridge is sealed without the use of loose sealing caps.

It is yet another advantage of the present invention that it provides improved organization and identification of many colors or shades, avoiding confusion by the dentist.

It is still another advantage of the present invention that the secure horizontal placement of the cartridge within the tray facilitates printing of identifying indicia thereon.

It is a feature of the present invention that the single patient dose cartridges are frictionally held in place.

It is yet another feature of the present invention that an angled portion of the tray is adapted to securely receive and seal the discharge nozzle of a dental cartridge.

These and other objects, advantages, and features will become readily apparent in view of the following more detailed description.

BRIEF DESCRIPTION OF THE DRAWINGS

FIG. 8 is a cross section taken along lines 8—8 in FIG. 6.

FIG. 9 is a partial cross section taken along lines 9—9 in FIG. 6.

FIG. 14 is a plan view with a partial section illustrating another embodiment of the present invention.

FIG. 15 is a cross section taken along line 15—15 in FIG. 14.

DETAIL DESCRIPTION OF THE PREFERRED EMBODIMENTS

Figure 1:
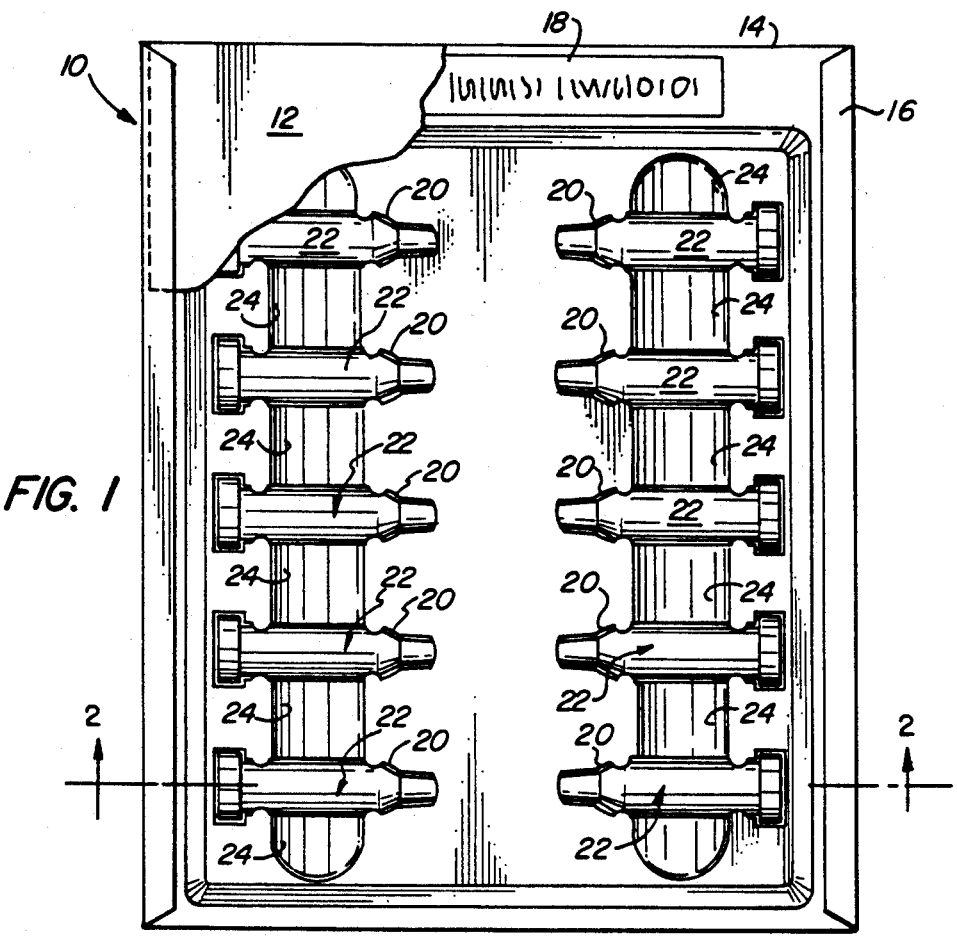
FIG. 1 is a plan view with a partial section of one embodiment of the present invention.

FIG. 1 illustrates one embodiment of the present invention. Tray assembly 10 comprises a tray body 14 having a bottom or seat forming surface 14A and a sliding cover 12 cut away to illustrate the interior seat forming surface of formed tray 14. Tray 14 includes circumscribing end walls and lateral flange 16A having a lip 16 or trackway along the opposed longitudinal ends thereof that receives cover 12 and permits cover 12 to slide therein. Therefore, the contents of tray 14 can be covered and yet be easily accessible. Formed within tray 14 are a plurality of cartridge or capsule seats or wells 20. Each of cartridge seats or wells 20 contain a unit dose cartridge 22 having dental material therein. The cover 12 is adapted to slide slightly above the top surface of the cartridges 22 placed within tray 14. This prevents cartridges 22 from being unintentionally dislodged from the cartridge seats 20 formed within during shipment or rough handling. Identifying indicia 18 may be placed on the top surface of tray 14 as well as on the cover 12. This identifying indicia 18 indicates the type of material and/or shade contained in the cartridges 22 placed within tray 14. If the dental material contained within the cartridges 22 is of the light activated type, the cartridge 22, tray 14, and cover 12 are made of an opaque material or of a material having the ability to block the wavelength of light that cures the light activated dental material. Adjacent each cartridge and running longitudinally are finger notches or wells 24. The tray as illustrated has two columns with each column containing five cartridges 22. Therefore, ten cartridges 22 can be held in a single tray. Accordingly, the tray thus functions as a self counting means whereby an operator need not be concerned with counting the number of capsules, as would be required with the conventional packages previously used for packaging such capsules. However, the number of columns or cartridges 22 held by tray 14 can vary, depending upon the particular application and/or size of the tray. The finger notches or wells 24 permit easy access to the cartridges 22 placed within the cartridge wells 20. The tray 14 can be easily made using conventional molding techniques, e.g. as vacuum forming. The tray 14 is made of plastic, and when light activated dental material is contained within cartridge 22, is made of an opaque plastic or of a material having the ability to block the wavelength of light that cures the light activated dental material.

Figure 2:
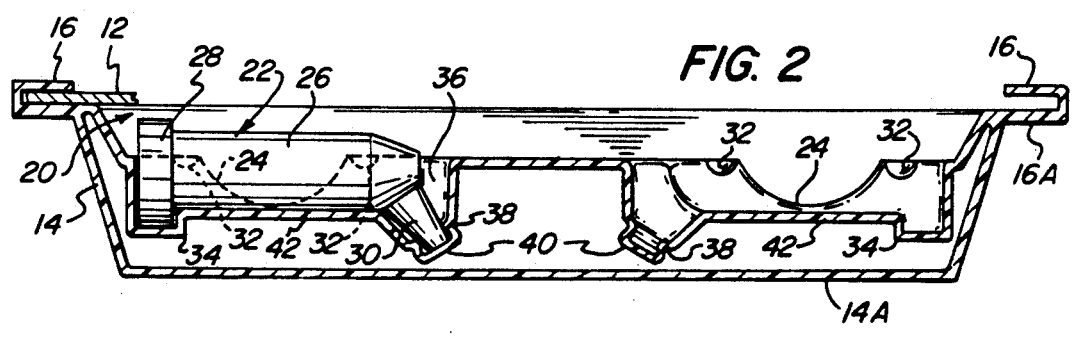
FIG. 2 is a cross section taken along line 2—2 in FIG. 1.

FIG. 2 illustrates a cross section of the present invention taken along line 2—2 in FIG. 1. A cartridge 22 can clearly be seen placed within the well 20. The cartridge 22 is made of a cylindrical cartridge body 26, which contains a reservoir of dental material. At the open end thereof is a flange 28. In this end a piston or plug, not shown, is placed, which seals this end and is used to force the dental material out of the cartridge 22 when the piston is displaced. The other end of cartridge 22 is closed by a suitable end wall and is provided with an angularly disposed open discharge nozzle 30. The cartridge body 26 is retained by a snap fit within well 20 by fingers 32. Fingers 32 protrude into a portion of well 20 such that a snap or friction fit is formed holding cartridge 22 within the well portion 20. This is accomplished by the fingers 32 extending above the longitudinal axis of the cylindrical body portion 26 such that a gap between adjacent pairs of fingers 32 is less than the outside diameter of body portion 26. The snap fit may also be provided by having the side walls of the recess defining the seat circumscribing the body portion of the capsule extend slightly beyond the longitudinal axis of the capsule.

A flange well portion 34 is formed as part of cartridge well 20 to accommodate the capsule flange 28. A nozzle well portion 36 is also formed as part of the cartridge well 20 for receiving the nozzle of the capsule. The nozzle well portion 36 has a nozzle seal 38 thereon. Nozzle seal 38 forms a circumferential seal about the side walls of nozzle 30. This circumferential nozzle seal 38 is in addition to a nozzle well bottom seal 40 formed at the bottom of the nozzle well 36. The nozzle well bottom seal 40 is angled by the appropriate amount to rest flush against the open or discharge end of nozzle 30. This angle will depend upon the angle of the nozzle 30 with respect to the longitudinal axis of body portion 26. However, this angle is generally 45 degrees with respect to the horizontal surface of the tray 14. Between the flange well portion 34 and the nozzle well portion 36 is body well portion 42. The body portion 26 of cartridge 20 rests along the surface of body well portion 42. Therefore, the cartridge 22 is firmly held horizontally in place with the end of nozzle 30 resting securely adjacent nozzle well bottom 40. This prevents contamination from entering the open end of nozzle 30. The tray 14 can be formed from a material that is opaque, or of a material having the ability to block the wavelength of light that cures the light activated dental material, thereby preventing the exposure of the dental material to light, should it be of the light activated type. FIG. 2 additionally illustrates the finger notches or wells 24 which permits the grasping of the body portion 26 of the capsule by the dentist to remove the cartridge 22 from the tray 14 for use in a dental syringe gun (not shown).

Figure 3:
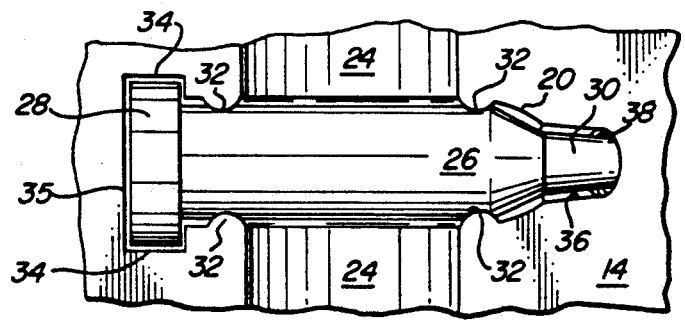
FIG. 3 is an enlarged portion of a plan view of the invention.

FIG. 3 more clearly illustrates the fingers 32 used to securely hold the cartridge body 26 into the cartridge well 20. The fingers 32 protrude into the cartridge well 20 such that the distance between adjacent pairs is less than the outside diameter of cartridge body 26. Thereby, a snap fit, or friction fit, is formed securely holding the cartridge in place. The longitudinal displacement of cartridge 22 is additionally prevented by flange well portion 34 and nozzle well portion 36. The flange well portion 34 has a rear surface 35 adjacent the cartridge flange 28 that is slightly angled. Thereby, when placing the cartridge within the cartridge well 20, the rear end of flange 28 strikes the rear surface 35 of flange well 34 forcing it forward resulting in the nozzle 30 being forced forward, making contact with the nozzle well bottom 40. This will assure the complete contact of the open nozzle 30 with the nozzle well bottom 40 providing a secure seal. The tray 14 also produces a secure platform for the cartridges 22 preventing rotation so as to permit each cartridge 22 to be printed, if desired, with identifying indicia thereon while in the tray 14. This is accomplished with a single pad printer that prints on all the cartridges 22 in the tray in a single step. This greatly saves printing time if it is desired to print each cartridge 22 with identifying indicia.

Figure 4:
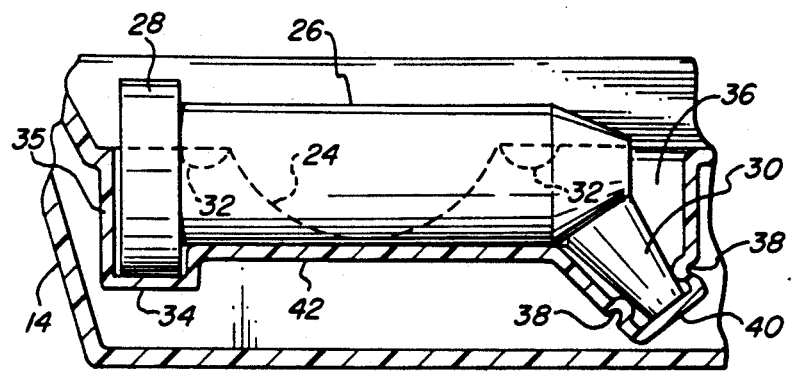
FIG. 4 is an enlarged portion of a cross section of the invention.

FIG. 4 is an enlarged view more clearly illustrating the cross section of a single cartridge well 20. In this view, the nozzle well bottom seal 40 and the nozzle circumferential seal 38 can be more clearly seen. The slight angle attributed to rear surface 35 is used to force the cartridge 22 slightly forward assuring contact between the nozzle well bottom 40 and open nozzle 30, can also more clearly be seen.

Figure 5:
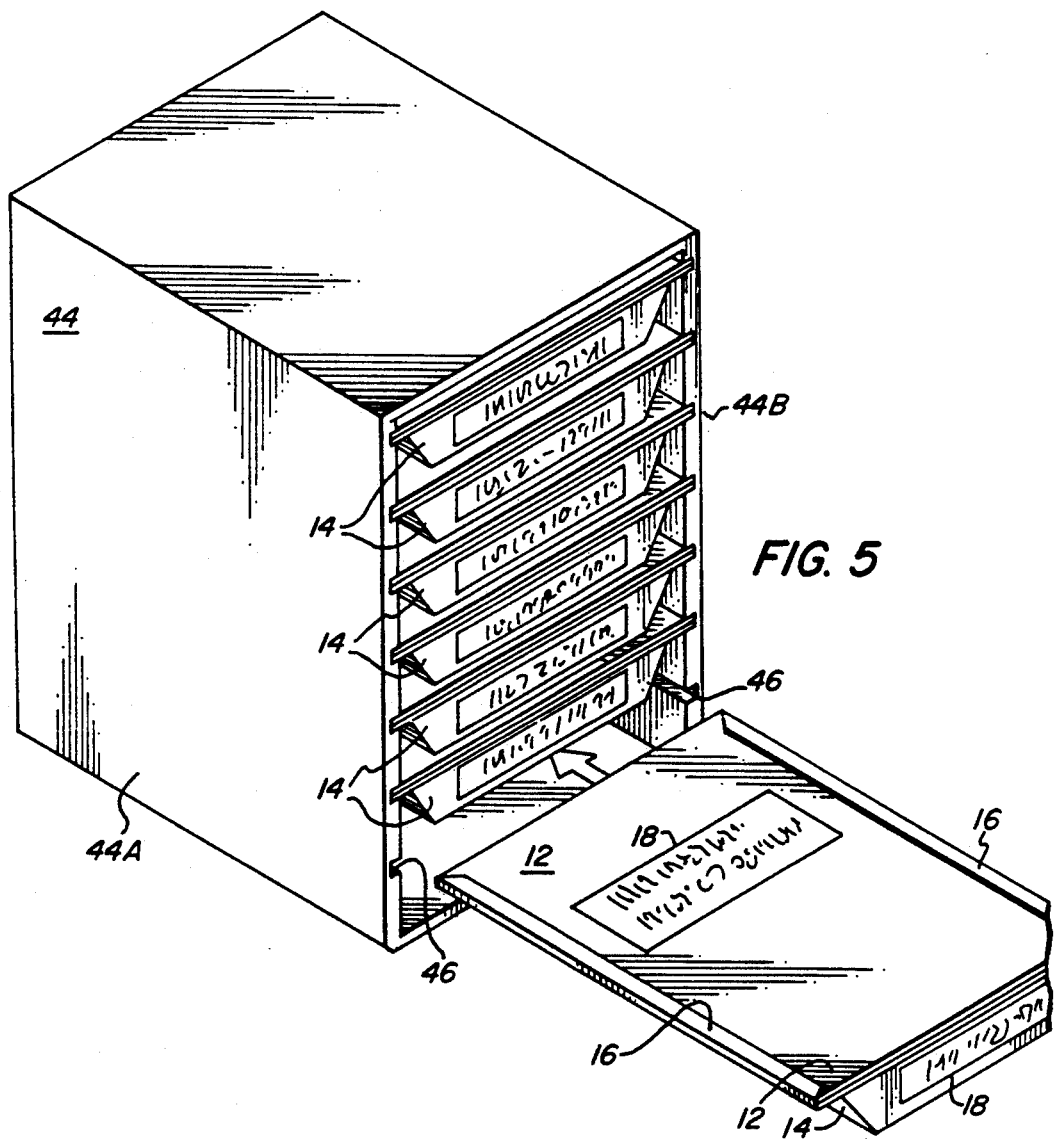
FIG. 5 is a perspective view of one embodiment of the rack system of the invention.

FIG. 5 illustrates a system for organizing a plurality of trays 14 when used in a system that has a number of colors or shades of dental material. A rack 44 has a plurality of grooves 46 formed in the opposed side walls 44A, 44B, such that the flange 16A of trays 14 can slide therein. This effectively stacks each tray, saving considerable space and yet makes each tray individually accessible to select the material, color, or shade desired. A single color or shade of dental material can be used for each tray. This permits the dentist to maintain an inventory of numerous colors that can easily and quickly be selected. Identifying indicia 18 is placed on the sliding cover 12, as well as on the surface of tray 14.

Figure 6:
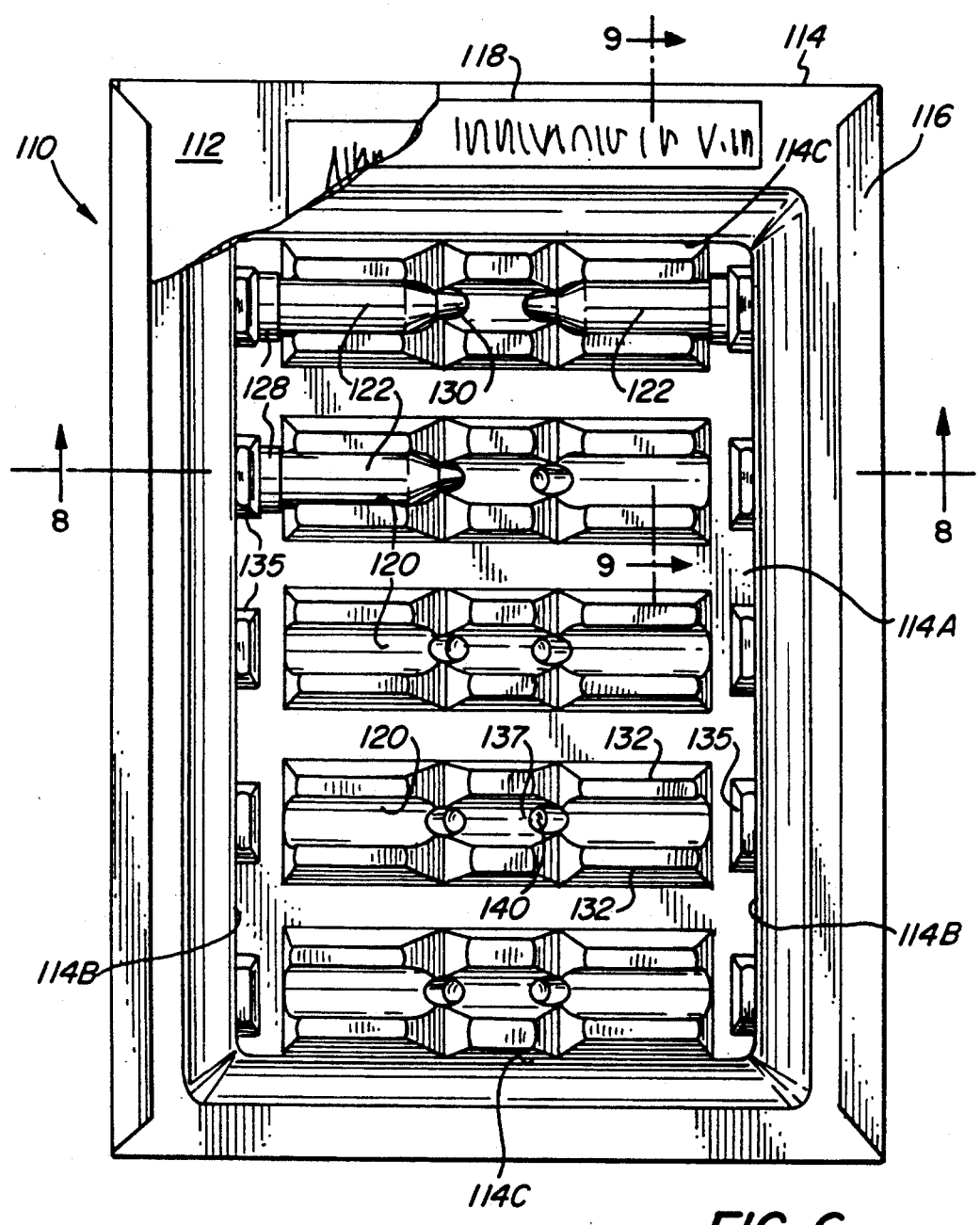
FIG. 6 is a plan view with a partial section of another embodiment of the invention.

FIGS. 6-11 illustrate another embodiment of the present invention. FIG. 6 illustrates the present invention having a slightly different configuration for retaining the cartridges 22 than illustrated in FIGS. 1-4 in the previous embodiment. In FIG. 6, a tray assembly 110 is illustrated having a sliding cover 112. The tray 114 is formed from a thin plastic material. This can be done by any conventional means such as vacuum forming. The tray includes bottom wall 114A having opposed side and end walls 114B and 114C respectively. The end walls 114B, 114B of the tray 114 has a flanged channel or lip 116 used to retain sliding cover 112. Identifying indicia 118 may be placed on the tray 114 to identify the contents of the cartridges 22 contained therein. The tray 114 has cartridge wells 120 integrally formed on the bottom wall 114A. Within each cartridge well 120 is placed a unit dose cartridge 122. Surrounding a portion of the cartridge 22 are flexible sides 132 which are performed as an integral part of the bottom wall 114A. The flexible sides permit the cartridge 22 to be retained therebetween by a snap or friction fit within the cartridge well 120. The cartridge 22 has a flange 28 retained by a rear wall 135 of the cartridge well. The cartridge 22 has an angularly disposed nozzle 30 which is sealed by nozzle well bottom seal 140 and retained by nozzle stop 137.

Figure 7:
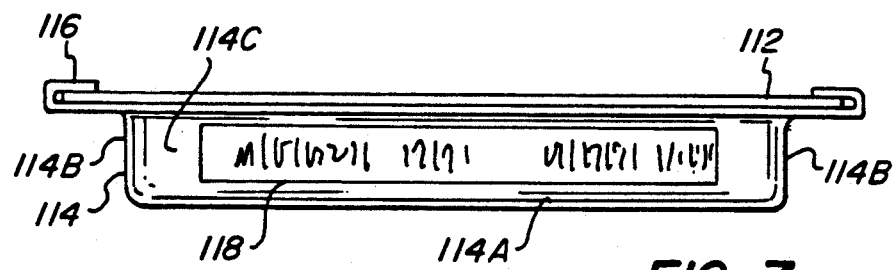
FIG. 7 is a front elevational view.

FIG. 7 illustrates a front elevational view of the present invention. Identifying indicia 118 may be placed on the front end surface of tray 114. From this figure, it should be appreciated that the tray 114 has a relatively low profile and, therefore, is very conducive to stacking. Additionally, the sliding cover 112 comes into close contact with the cartridges 22 placed within tray 114 preventing them from being unintentionally dislodged from their respective seats or wells during shipping or rough handling.

FIG. 8 more clearly illustrates the embodiment of the present invention illustrated in FIG. 6. In FIG. 8, the cartridge 22 can clearly be seen having a body 26, a flange 28, and an angularly disposed nozzle 30. Flexible sides 132 help retain the cartridge 22 within the tray 114. The cartridge 22 can easily be removed from the tray 114 by grasping the cartridge by the rear flange 28 and by the front end adjacent nozzle 30. Finger areas or notches formed in the flexible sides 132 may be provided as seen at 124 for grasping the cartridge 22. The cartridge well 120 is comprised of a flange well portion 134, a body well portion 142, and a nozzle well portion 136. The flange well portion 134 has associated therewith a rear wall 135. Rear wall 135 is angled slightly so as to contact flange 28 and advance it forward. This helps in positioning the cartridge within the well and securing and sealing the nozzle 30 within the nozzle well portion 136 by means of the comprising nozzle stop 137 and nozzle well bottom seal 140. The bottom seal 140 abuts against the open end of nozzle 30, effectively sealing it from dirt, contamination, or light. The nozzle stop 137 helps prevent the nozzle 130 from riding up the angled bottom seal 140. In the embodiment illustrated in FIG. 8, the open nozzle 30 is easily placed within the tray 114, which securely holds and seals it.

In operation, the nozzle 30 of cartridge 22 is placed within the nozzle portion 136. The flange 28 can then be pushed downward, locking the body portion 26 between the flexible sides 132, while the angled rear wall 135 advances the flange 28 slightly forward, which in turn forces the open end of nozzle 30 securely against nozzle bottom seal 140. This locking of the nozzle prevents rotation of the cartridge and allows the tray 114 to be used as a support for pad printing all of the individual cartridges 22 contained therein, if desired. This greatly facilitates printing and saves considerable time and expense.

FIG. 9 more clearly illustrates the positioning of the cartridge 22 between the flexible sides 132. Body portion 26 of cartridge 22 can clearly be seen between the flexible sides 132. Flexible sides 132 extend above the center of body portion 26. The top gap or space between adjacent flexible sides 132 is less than the outside diameter of body portion 26. Therefore, when body portion 26 is forced between flexible sides 132, the sides deflect outward until the widest diameter of body portion 26 passes therethrough, at which point the flexible sides 132 "snap" back into their normal position. In this way, the body portion 26 is securely held within the tray 114.

Figure 10:
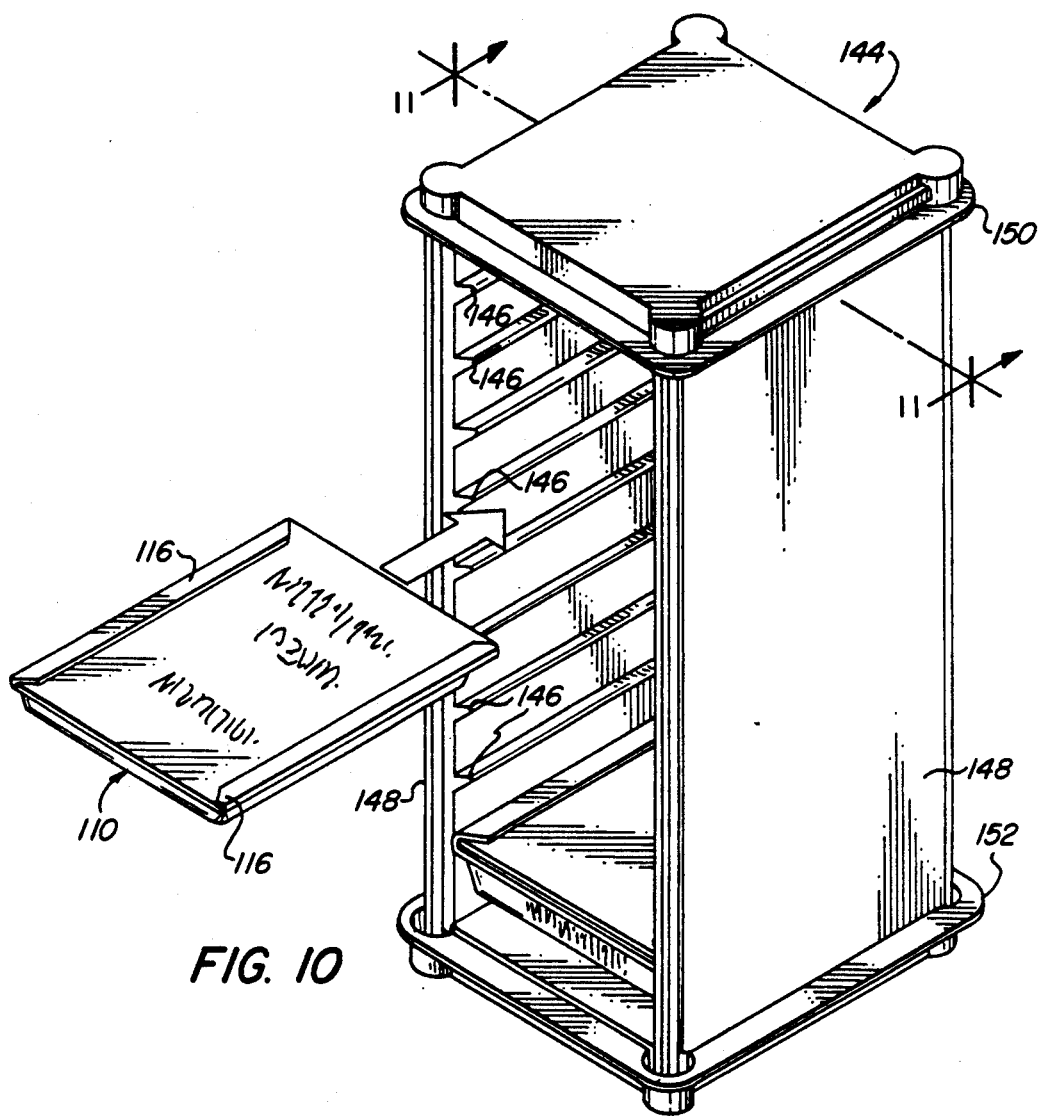
FIG. 10 is a perspective view of another embodiment of the rack system of the present invention.
Figure 11:
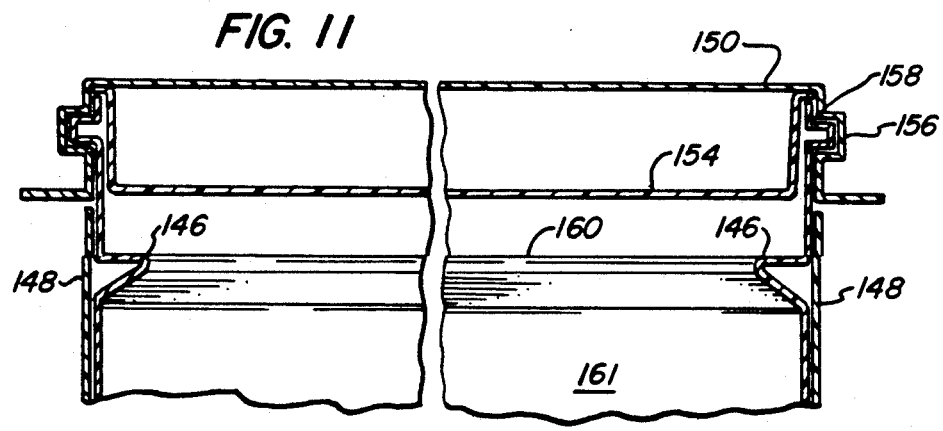
FIG. 11 is a partial cross section taken along line 11—11 in FIG. 10.

FIGS. 10-11 illustrate a rack system for organizing the tray assemblies 110 for providing a dentist with an organization system whereby numerous colors or shades of dental material can be organized for easy retrieval and application to a patient. A plurality of tray assemblies 110 are stacked in a rack system. The rack system comprises at least one rack assembly 144. Rack assembly 144 has opposed sides 148 having formed slides 146 contained therein. The slides 146 permit the lip or channel 116 of tray assembly 110 to slide thereon. In the illustrated embodiment, rack 144 comprises opposed sides 148, 148 having interconnected therebetween a back wall 148A. The opposed side walls 148, 148 are connected to the back wall 148A by a flexible integrally formed hinge 148B, 148B. Thus, the sides and back walls of the rack can be shipped in a knock down arrangement which can be readily erected by the user.

Figure 12:
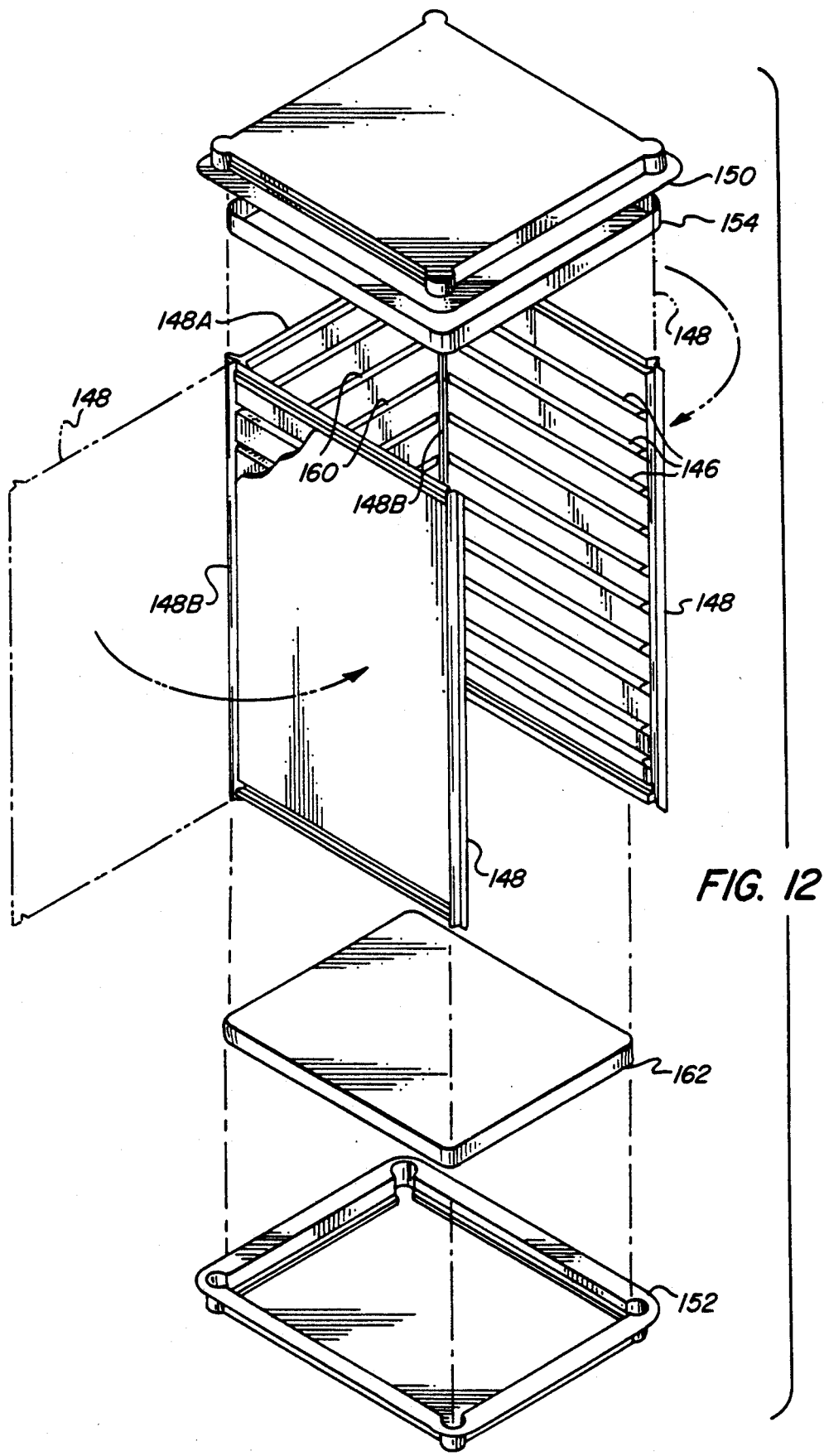
FIG. 12 is an exploded perspective view of the rack system of the invention illustrating assembly.

FIG. 11 more clearly illustrates the construction or assembly of rack assembly 144. The top 150 is attached to sides 148 by inserting the upper edges of the side walls 148 and back wall 148A into a top locking groove 156 formed along the opposed and back sides of the top 150. Top insert 154 functions to lock the top and side walls between it and the top 150, and provides a finished appearance as well as better structural integrity to the assembled rack. A bottom wall 152 is similarly connected to the bottom edge of the side walls 148, 148 and back wall 148A; and a bottom insert 162 function to lock the side and back walls 148, 148 and 148A between the insert 162 and the bottom wall 152. The rack slides 146 can more clearly be seen in FIG. 11. The slides 146 are conveniently and inexpensively formed within the sides 148. Also, a back ledge 160 is formed in back 148A to further support the tray assembly 110. The rack assembly 114 is manufactured by conventional vacuum forming or any other similar process. In this way, the rack assembly 144 is made very inexpensively, thereby providing an efficient organizational system for the dentist with minimal cost. The rack assembly 144 can be shipped flat and easily assembled or snapped together. This is more clearly illustrated in FIG. 12. The sides 148 are shown in phanton flat. The sides 148 are then folded inward during assembly. A bottom insert 162 is also used to provide a finished apparatus and structural integrity. Cartridges 22 containing a single shade or color of material can be placed in a single tray assembly 110. This permits the dentist to quickly and efficiently organize dental material by the numerous shades and colors that are available. The dentist can therefore quickly provide a patient with the best color match for a particular dental procedure.

Figure 13:
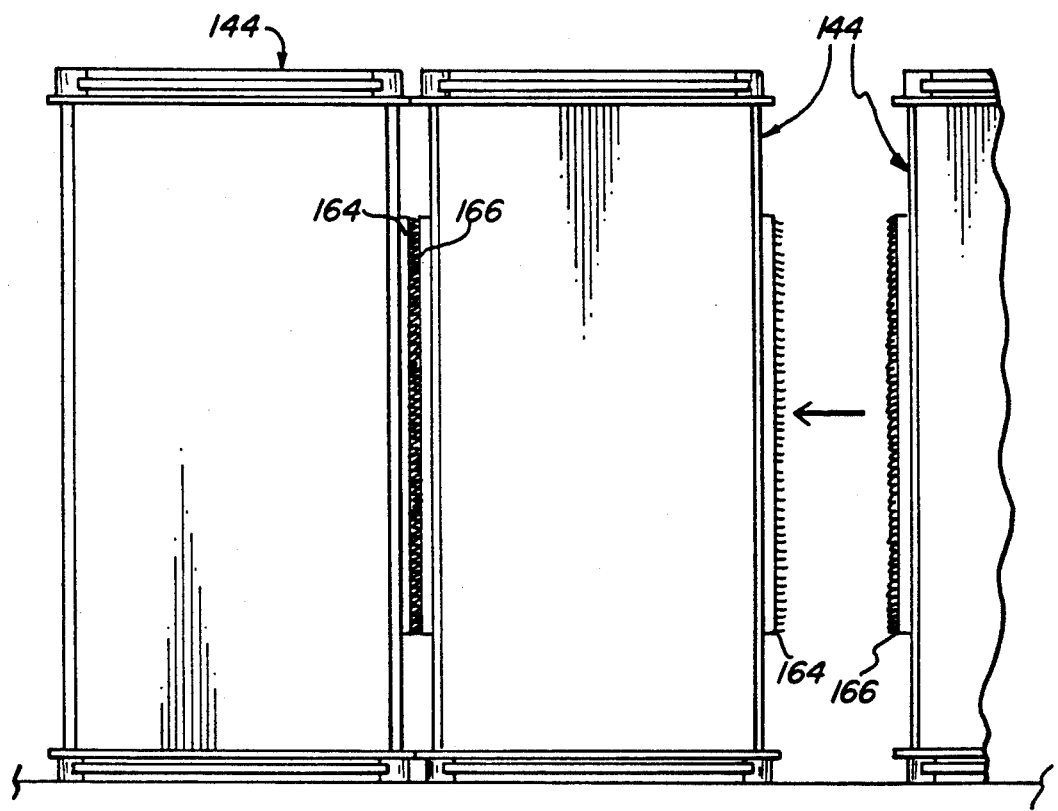
FIG. 13 is a front elevational view illustrating an element of the present invention.

Additionally, as illustrated in FIG. 13, the rack assemblies 144 are conveniently made to lock together forming an integral organizing system for a plurality of rack assemblies 114 disposed in side by side relationship. The rack assemblies 114, illustrated in FIG. 13, are attached together by means of hook fasteners 164 and complementary loop fasteners 166. The hook and loop fasteners 164 and 166 are commonly available and sold under the trademark Velcro. The rack assemblies can either be assembled horizontally as shown or vertically.

FIGS. 14 and 15 illustrate a third embodiment of the present invention. In FIG. 14, a circular tray assembly 210 is illustrated. Circular tray assembly 210 has a circular formed tray 214 comprised of a bottom wall and a circumscribing end wall extending upwardly therefrom. A rotating cover 213 is attached to circular formed tray 214 by pivot 217 connected to an embossment 217A formed integrally of the bottom wall. An opening 215 is provided in the cover 213. The opening 215 is sized to receive a segmental raised tray portion 219 spaced above the bottom wall. The raised tray portion 219 is a blank portion that is used to seal the opening 215 in the closed position, yet provide easy rotation of the cover 213 so that the opening 215 can expose the contents within the tray 214 when the cover is rotated. Formed within tray 214 are a plurality of radially extending cartridge wells 220. Cartridge wells 220 are adapted to receive a unit dose cartridge 22. The cartridge wells 220 are formed by flexible sides 232 and rear wall 235 which are integrally formed in the bottom wall.

FIG. 15 more clearly illustrates the placement of a cartridge 22 within the formed tray 214. The cartridge 22 is comprised of a body 26 having a flange 28 on one end thereof an open angularly disposed nozzle 30 on the other. The cartridge 22 is secured horizontally within the cartridge well 220 which is formed in tray 214. The cartridge well 220 is formed by the flexible side walls 232, the flange well portion 234, the body portion 242, and the nozzle well portion 236. The nozzle well portion 236 comprised of a nozzle bottom seal 240 and a nozzle stop 237. When a cartridge 22 is placed in the cartridge well 220, the flexible sides 232 in combination with the nozzle well 236 and flange well 234 securely hold the cartridge 22 therein. The rear wall 235 abuts against flange 28 forcing the cartridge 22 slightly forward assuring complete sealing of the nozzle 30.

The rotating cover 213 illustrated in FIGS. 14 and 15 is shown in the closed position. The raised tray portion 219 extends through and slightly above the opening 215. Thereby, the cover is prevented from being inadvertently rotated to an open position. However, when a cartridge is intended to be removed from the tray assembly 210, the rotating cover 213 can easily be rotated by sliding the opening over the raised portion 219 to expose a cartridge 22 which is to be removed from the tray 214 prior to application with a dental gun, not shown, for application to a patient. Identifying indicia can also be placed on the raised portion 219 to identify the contents of the tray assembly 210 or upon the rotating cover. The tray assembly 210 is made of an opaque material when light activated dental material is contained within the cartridges 22 placed therein. Alternatively, the tray assembly 210 can be made of material that is not transparent to the wavelengths of light used to cure the dental material contained therein, but yet transparent to at least a portion of the visible light spectrum. This permits the dentist to easily view the contents of the package without opening the tray assembly 210. Thereby, the dentist can quickly appraise the remaining inventory of material without opening the cover 213. The raised tray portion 219 has the additional advantage in more securely preventing light from inadvertently entering the tray assembly 210 during storage. As in the other embodiments, the embodiment illustrated in FIGS. 14 and 15 can easily be made inexpensively by well known vacuum forming procedures.

The above described invention greatly facilitates the use by the dentist of pre-dosed patient cartridges and provides a convenient system for efficiently organizing the many different colors and shades of dental material that are available.

While the invention has been described with respect to several embodiments, it should be understood and appreciated that modifications may be made without departing from the spirit and scope of this invention.

What is claimed is:

1. A dental cartridge package comprising:
   a tray;
   a plurality of wells formed within said tray, each of said plurality of wells formed to receive a cartridge having a flange, body, and angularly disposed nozzle portion;
   means, associated with each of said plurality of wells, for securing a cartridge therein;
   a bottom surface, associated with each of said plurality of wells, angled to abut the open end of an angularly disposed nozzle portion whereby dirt and light are prevented from entering; and means, associated with each of said plurality of wells, for guiding a cartridge such that an angularly disposed nozzle portion securely abuts said means for sealing.

2. A dental package as in claim 1 wherein:
said means for securing a cartridge forms a friction fit with a body of a cartridge.

3. A package as in claim 1 further comprising:
a finger well adjacent each said plurality of depresions.

4. A dental cartridge package comprising:
a tray;
said tray having a plurality of cartridge wells formed to receive a single patient dose cartridge having a flange, body, and angularly disposed nozzle;
a plurality of pairs of flexible sides, one each of said plurality of pairs of flexible sides associated with one each of said plurality of wells, each of said plurality of pairs of flexible sides longitudinally receiving and laterally holding a body of a cartridge;
a plurality of nozzle wells, one each of said plurality of nozzle wells associated with one each of said plurality of cartridge wells formed to receive and seal an angularly disposed nozzle of a cartridge;
a plurality of flange wells formed within said tray formed to receive a flange of a cartridge;
a plurality of rear walls formed within said tray, each one of said plurality of rear walls positioned adjacent each one of said plurality of flange wells, such that when a cartridge is placed in one of said plurality of cartridge wells, a flange of a cartridge is guided by one of said plurality of rear walls; and
a plurality of nozzle stops, each one of said plurality of nozzle stops adjacent one of said plurality of nozzle wells, whereby a cartridge is held longitudinally in position securely sealing a nozzle of a cartridge.

5. A dental tray as in claim 4 further comprising:
a channel placed along each longitudinal edge of said tray; and
a cover sliding within each said channel.

6. A dental tray as in claim 5 further comprising:
identifying indicia placed on said tray and said cover.

7. A dental tray as in claim 6 wherein:
said identifying indicia identifies the material and shade of material contained within the cartridge.

8. A dental package comprising:
a tray;
a plurality of single patient dose cartridges containing dental material and having a flange, a body, and an angularly disposed discharge nozzle;
a plurality of cartridge body wells placed within said tray, each one of said plurality of cartridge body wells formed to longitudinally receive and securely hold laterally a body of one of said plurality of single patient dose cartridges;
a plurality of nozzle wells, each one of said plurality of nozzle wells formed to receive and seal an angularly disposed nozzle of one of said plurality of cartridges;
means, associated with each one of said plurality of cartridge body and nozzle wells, for preventing longitudinal movement of one said plurality of single patient dose cartridges; and a cover sliding onto said tray covering said plurality of single patient dose cartridges preventing their unintentional dislodgement from said tray.

9. A dental cartridge package for holding a plurality of single patient dose dental cartridges having a tubular body, a flange at one end, and an open angularly disposed nozzle at the other end comprising:
a plastic tray;
a plurality of body wells formed within said tray formed to hold a body of a dental cartridge horizontally along the longitudinal axis thereof;
a plurality of nozzle wells formed to receive an angularly disposed nozzle of a dental cartridge;
a plurality of nozzle seals, one of said plurality of nozzle seals at the bottom of each of said plurality of nozzle wells angled to flushly abut an open nozzle;
a plurality of nozzle stops, one of said plurality of nozzle stops adjacent each of said plurality of nozzle seals;
a plurality of angled rear surfaces, one of said plurality of angled rear surfaces associated with each of said plurality of body wells whereby a flange of a dental cartridge strikes one of said angled rear surfaces and is forced forward against one of said plurality of nozzle seals; and
a tray cover.

10. A dental tray as in claim 9 wherein:
said tray is opaque.

11. A dental tray as in claim 10 wherein:
said cover is made of a material that blocks wavelengths of light that are used to cure dental material contained within a cartridge, yet permits a portion of visible light spectrum wavelengths to pass therethrough.

12. A package for counting, storing, shipping and dispensing a capsule comprising:
a tray having a capsule supporting wall and an upwardly extending circumscribing end wall,
said end wall terminating at the upper end thereof in a laterally outwardly extending flange;
said flange being reversely bent to define a trackway;
means integrally formed on said capsule supporting wall defining a predetermined number of capsule seats;
each such seat including opposed flexible sides formed of the material of said supporting wall and extending upwardly therefrom to define a cradle for receiving a capsule;
said flexible sides conforming to the diameter of a capsule adapted to be received therein;
and said flexible sides being spaced at their upper end a distance slightly less than the diameter of a capsule whereby a capsule is fictionally retained therein by a snap fit,
said seat including a flange recess at one end thereof;
and a nozzle recess at the other end thereof;
said nozzle recess being formed to effectively seal a nozzle of a capsule retained in said seat;
and a closure slidable disposed in said trackway;
said circumscribing end wall extending upwardly to a point slightly above a body of a capsule retained in said seat whereby said closure prohibits capsules from being inadvertently dislodged from its respective seat.

13. A dental cartridge package as in claim 9 wherein:
said plastic tray is circular in shape.

14. A dental cartridge package as in claim 13 wherein:
said tray cover is rotatably attached to said tray, said cover having an opening therein, whereby said opening can be rotated into position exposing a dental cartridge for removal from said tray.

15. A dental container as in claim 14 further comprising:
a raised portion on said tray fitting within said opening, whereby said cover can be rotated and held in position.

* * * * *